United States Patent [19]

Schudok et al.

[11] Patent Number: 5,756,321
[45] Date of Patent: May 26, 1998

[54] PROCESS FOR ENZYMATIC ACYLATION OF ALCOHOLS WITH ALKOXYVINYL ACETATES BY TRANSESTERIFICATION

[75] Inventors: Manfred Schudok, Hattersheim; Gerhard Kretzschmar, Eschborn, both of Germany

[73] Assignee: Hoechst Aktiengesellschaft, Germany

[21] Appl. No.: 603,311

[22] Filed: Feb. 20, 1996

[30] Foreign Application Priority Data

Feb. 20, 1995 [DE] Germany .................. 195 05 672.8

[51] Int. Cl.$^6$ .............................. C12N 9/20; C12P 41/00; C12P 7/62
[52] U.S. Cl. .................. 435/123; 435/128; 435/134; 435/135; 435/155; 435/158; 435/198; 435/280; 435/874; 435/922
[58] Field of Search ................ 435/135, 134, 435/155, 198, 874, 922, 280, 123, 128, 158

[56] References Cited

U.S. PATENT DOCUMENTS

| | | | |
|---|---|---|---|
| 4,963,492 | 10/1990 | Keller et al. | 435/155 |
| 5,387,514 | 2/1995 | Schudok et al. | 435/135 |

FOREIGN PATENT DOCUMENTS

| | | |
|---|---|---|
| 0 321 918 | 6/1989 | European Pat. Off. |
| 0 492 497 | 7/1992 | European Pat. Off. |
| 0 507 278 | 10/1992 | European Pat. Off. |
| 0 577 446 | 1/1994 | European Pat. Off. |

OTHER PUBLICATIONS

M. Degueil–Castaing et al., "Enzymatic Reactions in Organic Synthesis: 2–Ester Interchange of Vinyl Esters", *Tetrahedron Lett* 28(9): 953–954 (1987).

Bruneau et al., "Ruthenium–Catalysed Additions to Alkynes: Synthesis of Activated Esters and Their Use in Acylation Reactions", National Institute of Health Library, pp. 755–763, Feb. 22, 1993.

Y. Kita et al., "Novel Efficient Synthesis of 1–Ethoxyvinyl Esters Using Ruthenium Catalysts and their Use in Acylation of Amines and Alcohols: Synthese of Hydrophilic 3'–N–Acylated Oxaunomycin Derivatives", *J. Chem. Soc. Perkin Trans.* 1: 2999–30005 (1993).

Y. Kita et al., "A Novel Efficient Synthesis of 1–Ethoxyvinyl Esters and Thei Use in Acylation of Amines and Alcohols: Synthesis of Water–Soluble Oxaunomycin Derivatives", *SYNLETT* pp. 273–274 (1993).

J. Arens, "The Chemistry of Acetylenic Ethers XIII. Acetylenic ethers as reagents for the preparation of amides", *Recueil Chem. Pays Bas.* 74: 769–770 (1955).

Z. Kabouche et al., "Enol Esters as Intermediates for the Facile Conversion of Amino Acids into Amides and Dipeptides", *Tetrahedron Letters* 32(39): 5359–5362 (1991).

Kita et al. Tetrahedron Letters vol. 37 No. 41 pp. 7369–7372, 7 Oct. 1996.

*Primary Examiner*—Herbert J. Lilling
*Attorney, Agent, or Firm*—Foley & Lardner

[57] ABSTRACT

Methods for the enzyme catalyzed acylation of primary and secondary alcohols using an enol ester as the acyl donor are described. The acylation occurs in organic media, and is enantioselective for racemic or prochiral alcohols. The reaction is irreversible, and produces unreactive by-products.

19 Claims, No Drawings

PROCESS FOR ENZYMATIC ACYLATION OF ALCOHOLS WITH ALKOXYVINYL ACETATES BY TRANSESTERIFICATION

FIELD OF THE INVENTION

This disclosure relates to methods for the enzyme-catalyzed stereoselective acylation of alcohols by transesterification using an acylated ketene hemiacetal (enol ester) as the acyl donor.

BACKGROUND OF THE INVENTION

Optically active alcohols are useful as important chiral precursors in the preparation of biologically active substances such as pharmaceuticals, natural products, plant protection agents, and liquid crystal components. An economical method for producing enantiomerically pure or enantiomerically enriched alcohols from prochiral or racemic alcohols is therefore of great importance.

Pharmacologically active compounds whose preparation is facilitated by the method of the present invention include, for example: non-steroidal antiinflammatory drugs (NSAIDs) such as ibuprofen and naproxen; betablockers such as nifenalol and penbutolol; bronchospasmolytics such as tolubuterol and bitolterol; antimycotics such as tioconazole; and pyrethroids such as allethrines. Other compounds include; tetramisole; tetrahydrozoline; (R)-tomoxetine; (S)-fluoxetine; prostaglandins; modified and unmodified carbohydrates, (for example glucals); and protease inhibitors, for example renin and HIV protease inhibitors.

A preferred method for preparing optically active alcohols would be via asymmetric acylation. The esters so produced are readily separated from the alcohol starting material, and may also be deprotected under mild conditions to liberate the enantiomerically pure or enantiomerically enriched alcohol. One method that would be particularly useful for stereoselective acylation of alcohols would be to use an enzyme to catalyze the acylation reaction. This would take advantage of the enzyme's stereoselectivity and also would allow acylation to be achieved under conditions that are much milder than traditional chemical acylation methods, thereby minimizing undesired side reactions. Enzymatic acylation occurs under extremely mild reaction conditions, and it is therefore particularly useful for preparing sensitive primary and secondary alcohols.

Previous methods for enzyme-catalyzed esterification of alcohols have used vinyl esters as the acyl donor. Thus, for example, porcine pancreatic lipase has been used as the enzyme catalyst. See, for example Degueil-Castaing et al., Tetrahedron Lett. 28:953 (1987). In this particular instance no stereoselectivity was observed in the final product, but resolution of racemic alcohols has been achieved by enzyme-catalyzed transesterification reaction using vinyl esters as the acyl donor. See, for example, published European Application EP 0 321 918 A2. The enzymes used were lipases isolated either from porcine liver and pancreas or from various microorganisms, and the preferred vinyl ester was vinyl acetate. High enantiomeric excesses were frequently achieved using this method to resolve racemic alcohols. No reaction was observed in the absence of the enzyme catalyst. These acylation methods have used enzyme catalysts in free solution or immobilized on solid supports. See, for example: EP 0 321 918 A2; EP 0 492 497; CA 2 058 185; EP 0 507 278; and CA 2 064 676. An advantage of using immobilized enzymes was found to be an increase in the long-term stability of the enzyme.

Acylation reactions using vinyl esters as the acyl donor produces vinyl alcohol as the initial by-product which, following tautomerization, produces acetaldehyde. Aldehydes are highly reactive compounds however, and potentially can react with a side variety of functional groups to form, for example, hemiacetals, acetals, and Schiff's bases. Schiff's base formation is particularly facile. See Larock, "Comprehensive Organic Transformations." Verlag Chemie, New York, 1989, pp. 398, 425, 426, 758, 759, 932.

Aldehyde reactions with proteins via Schiff's base formation can modify enzyme active sites and can cause protein polymerization and crosslinking, leading to irreversible modification of proteins. See, for example, Mozhaev et al., Advanced Drug Delivery Reviews 4:387 (1990). This side reaction can lead to deactivation of the enzyme, causing termination of the transesterification reaction. Thus, a rapid loss of activity of the free enzyme is often observed when repeated transesterifications are carried out using vinyl acetate. The use of immobilized enzymes that are stabilized by the polymeric matrix of the solid support can reduce the rate of deactivation. See, for example EP 0 507 278 and CA 2 064 676.

It is readily apparent, therefore, to one skilled in the art that an efficient process for acylating alcohols is desirable. It is further apparent that a method that does not release reactive components, such as aldehydes, during enzymatic transesterification is also desirable. Such a method would prevent the occurrence both of undesirable modifications of the enzyme catalyst and of other unwanted chemical side reactions.

SUMMARY OF THE INVENTION

It is therefore an object of the present invention to provide a method for the enzyme catalyzed acylation of primary and secondary alcohols, wherein an enol ester is used as the acyl donor, and where the reaction by-products are unreactive.

In accomplishing this object, there has been provided, in accordance with one aspect of the present invention, a method for the enzyme catalyzed acylation of alcohols, comprising contacting a mixture of an ester and an alcohol with a lipase, wherein the ester has the formula I

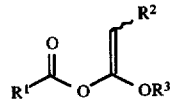

where $R^1$ is hydrogen, $C_1$–$C_{18}$-alkyl which is optionally substituted by halogen, phenyl or $(C_1$–$C_3)$-alkoxy $(C_1$–$C_4)$-alkyl, $R^2$ is hydrogen or E- or Z-methyl, and $R^3$ is methyl, ethyl, propyl, isopropyl or n-butyl; and where the alcohol has a formula selected from the group consisting of compounds having the formulae II and IV

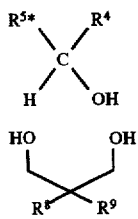

where $R^4$ is optionally halogen-substituted $C_1$–$C_{18}$-alkyl or $C_3$–$C_{10}$-cycloalkyl, $R^5$ is 2-epoxy-$C_1$–$C_5$-alkyl, or $R^5$ is $C_1$–$C_{10}$-alkyl, $C_2$–$C_{10}$-alkenyl, $C_2$–$C_{10}$-alkynyl or $C_3$–$C_8$-cycloalkenyl, optionally substituted with COOH, halogen, $NO_2$, CN, $C_1$–$C_4$-alkoxycarbonyl or phenyl, the phenyl group being optionally substituted with halogen, $NO_2$, CN or $C_1$–$C_4$-alkoxy, or $R^5$ is aryl or heteroaryl, optionally substituted with $C_1$–$C_4$-alkyl, $C_1$–$C_4$-alkoxy, halogen, $NO_2$, CN, or a protected amino group, or where $R^4$ and $R^5$ together form an alkenyl group having the formula III

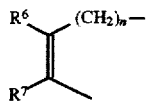

where n is 1, 2, or 3, and $R^6$ and $R^7$ are the same or different and each is hydrogen, $C_1$–$C_4$-alkyl, or $C_2$–$C_4$ alkenyl, $R^6$ and $R^7$ taken together are fused phenyl or fused naphthyl, optionally substituted with $C_1$–$C_4$-alkyl-, $C_1$–$C_4$-alkoxy-, $NO_2$—, CN— or halogen, and where the alkenyl group of formula III may optionally contain a keto group; $R^8$ is hydrogen or a $C_1$–$C_{18}$ alkyl group, $R^9$ is $C_1$–$C_{18}$ alkyl, aralkyl, aryl, benzyl, naphthylmethyl or O—$C_1$–$C_{18}$-alkyl, O-aralkyl, O-aryl, O-benzyl or O-naphthylmethyl.

In a preferred embodiment, the lipase is selected from the group consisting of lipases isolated from porcine liver, porcine pancreas, and microbial lipases. In a further preferred embodiment, the microbial lipase is isolated from a microorganism selected from the group consisting of Mucor, Rhizopus, Penicillium, Aspergillus, Candida, and Pseudomonas. In a still further preferred embodiment, the lipase is isolated from *Pseudomonas cepacia* or from *Candida antarctica*.

In another preferred embodiments of the invention, $R^1$ is $C_1$–$C_4$-alkyl, which is optionally chlorine-substituted, or $R^4$ is $C_1$–$C_7$-alkyl, which is optionally chlorine-substituted, or $R^1$ is methyl or chloromethyl.

In yet another preferred embodiment of the invention, $R^4$ is $C_3$–$C_5$-cycloalkyl, or $C_1$–$C_7$ alkyl which is optionally chlorine-substituted, or cyclopropyl. $R^4$ may also be optionally chlorine-substituted $C_1$–$C_5$-alkyl.

In still another preferred embodiment, $R^5$ is $C_1$–$C_4$-alkyl, $C_2$–$C_4$-alkenyl or $C_2$–$C_4$-alkynyl, where the alkyl, alkenyl or alkynyl radicals optionally are phenyl-substituted. $R^5$ may also be phenyl, naphthyl, phenanthryl, furyl, thienyl, pyrrolyl or pyridyl, optionally substituted with halogen, $NO_2$, CN, $C_1$–$C_4$-alkyl or $C_1$–$C_4$-alkoxy, or $R^5$ may be phenyl, naphthyl, phenanthryl, furyl or pyridyl, optionally substituted by $NO_2$ or methoxy.

In yet another preferred embodiment of the invention, $R^6$ and $R^7$ together form fused phenyl.

In a still further preferred embodiment of the invention, the acyl donor enol ester is methoxyvinyl acetate or ethoxyvinyl acetate.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION

The present invention provides a method for enzyme-catalyzed acylation of alcohols that is stereoselective and that does not produce reactive by-products that cause unwanted side reactions with other reagents or reaction products. The method uses acylated ketene hemiacetals (hereinafter "enol esters") as the acyl donor and a lipase as the enzyme catalyst. The method is suitable for resolution of racemic alcohols and for stereoselective acylation of prochiral alcohols. The method may also be used for the efficient acylation of achiral alcohols.

Enol esters suitable for the practice of the invention, such as ethoxyvinyl acetate, are not currently commercially available, but may be prepared by known methods. See, for example, Kita et al., *J. Chem. Soc. Perkin Trans.* 1, 1993:2999 ("Kita I"); Kita et al., *Synlett* 1993:273 ("Kita II"); and Bruneau et al., *Synlett* 1991:755, the disclosures of which are incorporated herein by reference.

A preferred starting material for the preparation of ethoxyvinyl acetate is ethoxyacetylene. Ethoxyacetylene and methoxyacetylene have previously both been employed as peptide coupling reagents. See, for example, Arens, *Recueil Chim. Pays Bas* 74:769 (1955). Activation of the carboxyl component with ethoxyacetylene or methoxy-acetylene forms an enol ester in situ, which then reacts with nucleophiles, such as amines or amino acids, to form the desired peptide linkage with concomitant release of ethyl acetate. The enol ester strongly activates the carboxyl group and, hence, the presence of an enzyme or other catalyst is unnecessary for the reaction to proceed. Aminolysis of isolated enol esters also takes place readily in the absence of a catalyst. See Kita (I and II) supra; Kabouche et al., *Tetrahedron Lett.* 32:5359 (1991); and Bruneau et al., supra.

In contrast to the case with amine nucleophiles, transesterification of enol esters by simple alcoholysis does not occur without the addition of a catalyst. A strong protic acid such as sulfuric acid or p-toluene sulfonic acid is typically added as a catalyst. See Kita (I and II), supra; and Bruneau et al., supra.

Unlike the situation with vinyl esters described supra, no reactive compounds such as aldehydes are released when enol esters react with nucleophiles. The only by-products formed from the enol esters are simple esters, such as ethyl acetate. These esters are themselves commonly employed as solvents for chemical reactions and enzymatic conversions. They furthermore are essentially inert under these reaction conditions and do not contribute to problematic side reactions by functioning as an acyl donor.

Surprisingly, it has now been found that enol esters such as ethoxyvinyl acetate can be employed as acyl donors in the enzyme-catalyzed O-acylation of primary and secondary alcohols. Acylation is not observed in the absence of the enzyme catalyst. Moreover, outstanding stereoselectivity is obtained in the acylation of racemic or prochiral alcohols, providing a method of achieving enantioselective acylation.

The present invention uses a lipase as the enzyme catalyst. Suitable lipases can be isolated, for example, from porcine liver, porcine pancreas or from microbial sources. Suitable microorganisms for isolating lipases include Mucor, Rhizopus, Penicillium, and Aspergillus. In a preferred embodiment of the invention the lipase is isolated from either Candida or Pseudomonas. Methods for isolating lipases are well-known to those of skill in the art. See, for example, Wills, *Advan. Lipid Res.* 3:197 (1965) and Desnuelle in *The Enzymes* Vol. 7, Boyer, Ed. (Academic Press, N.Y., 3 edn. 1972), p. 575. A wide variety of lipases are also commercially available from, for example, Sigma (St. Louis, Mo.), Calbiochem (La Jolla, Calif.), Boehringer Mannheim (Indianapolis, Ind.) or Amano (Nagoya, Japan).

The acylation reactions uses an enol ester as the acyl donor, where the enol ester has the formula I

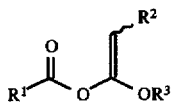

wherein

R$^1$ is hydrogen, C$_1$–C$_{18}$-alkyl optionally substituted by halogen, phenyl, (C$_1$–C$_3$)-alkoxy, or (C$_1$–C$_4$)-alkyl and R$^2$ is hydrogen or R$^2$ is an E- or Z- methyl group, and R$^3$ is methyl, ethyl, propyl, isopropyl or n-butyl.

The alcohol to be acylated has either the general formula II or formula IV:

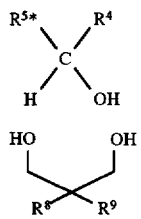

II

IV

In formula II R$^4$ can be C$_1$–C$_{18}$-alkyl or C$_3$–C$_{10}$-cycloalkyl, each of which can optionally be halogen-substituted, from monohalogenated to perhalogenated. R$^5$ can be epoxy-C$_1$–C$_5$-alkyl, where the epoxy group is β-to the OH group, or R$^5$ can alternatively be C$_1$–C$_{10}$-alkyl, C$_2$–C$_{10}$-alkenyl, C$_2$–C$_{10}$-alkynyl or C$_3$–C$_8$-cycloalkenyl. Each alkyl, alkenyl, alkynyl or cycloalkenyl group can optionally be substituted by COOH, halogen, NO$_2$, CN, C$_1$–C$_4$-alkoxycarbonyl or phenyl, and each phenyl group in turn can be optionally substituted by halogen, NO$_2$, CN or C$_1$–C$_4$-alkoxy. Alternatively, R$^4$ can be aryl or heteroaryl, where the aryl or heteroaryl groups also are optionally substituted by C$_1$–C$_4$-alkyl, C$_1$–C$_4$-alkoxy, halogen, NO$_2$, CN or a protected amino group. Suitable amino protecting groups are described in, for example, Greene, PROTECTIVE GROUPS IN ORGANIC SYNTHESIS, Wiley Interscience, New York, 1981, and include, but are not limited to Boc, Cbz, trifluoroacetyl, Fmoc, allyloxycarbonyl, and phthalimido.

R$^4$ and R$^5$ taken together can also be an alkenyl radical of the formula III:

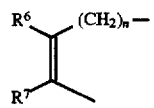

III

In formula III, n is 1, 2 or 3 and R$^6$ and R$^7$ can be identical or different and each is hydrogen, C$_2$–C$_4$-alkenyl, or C$_1$–C$_4$-alkyl. Alternatively R$^6$ and R$^7$ taken together can be fused phenyl or fused naphthyl, where the phenyl or naphthyl group is optionally substituted with C$_1$–C$_4$-alkyl-, C$_1$–C$_4$-alkoxy-, NO$_2$—, CN— or halogen. The alkenyl group of formula III may also contain a keto group.

In formula IV, R$^8$ can be hydrogen or an alkyl group and R$^9$ can be alkyl, aralkyl, aryl, benzyl, naphthylmethyl, O-alkyl, O-aralkyl, O-aryl, O-benzyl or O-naphthylmethyl.

The acylation reaction is carried out by mixing the reactants in a suitable solvent. Suitable solvents for carrying out the reaction include aqueous buffers and organic solvents well known to those of skill in the art. In a preferred embodiment of the invention, a non-polar organic solvent is used. Following completion of the reaction the enantiomerically enriched alcohol is then recovered. The optically pure ester may also be recovered.

In a preferred embodiment of the invention, R$^1$ is C$_1$–C$_4$-alkyl, optionally substituted by chlorine. More preferably, R$^1$ is methyl or chloromethyl. In another preferred embodiment R$^4$ is C$_1$–C$_7$-alkyl, optionally substituted by chlorine, or R$^4$ is C$_3$–C$_5$-cycloalkyl. More preferably R$^4$ is C$_1$–C$_5$-alkyl, optionally substituted by chlorine or R$^4$ is cyclopropyl.

In still another preferred embodiment, R$^5$ is C$_1$–C$_4$-alkyl, C$_2$–C$_4$-alkenyl or C$_2$–C$_4$-alkynyl, where each alkyl, alkenyl or alkynyl radicals is optionally phenyl-substituted or R$^5$ is phenyl, naphthyl, phenanthryl, furyl, thienyl, pyrrolyl or pyridyl, where each group is optionally substituted by halogen, NO$_2$, CN, C$_1$–C$_4$-alkyl or C$_1$–C$_4$-alkoxy. More preferably, R$^5$ is phenyl, naphthyl, phenanthryl, furyl or pyridyl, where each group is optionally substituted by NO$_2$ or methoxy. In yet another preferred embodiment, R$^6$ and R$^7$ taken together form fused phenyl.

In a preferred embodiment, the lipase used is isolated from a Pseudomonas species, preferably from *Pseudomonas cepacia*. In another preferred embodiment, the lipases are from a Candida species, preferably from *Candida antarctica*. Preferred esters according to formula I include methoxyvinyl acetate and ethoxyvinyl acetate.

The method according to the invention has several advantages compared to conventional processes for the resolution of alcohols, including that:

a) at least one enantiomer, and usually both, is always produced in optically pure form;

b) the enzyme catalyst is readily recovered or, alternatively, can be employed in immobilized form;

c) separation of the ester and alcohol products is very simple, for example by distillation or by chromatography;

d) the reaction can be carried out either in organic solvents or without solvent;

e) high conversion at rapid rates can be achieved, even using comparatively low amounts of enzyme;

f) in contrast to the use of vinyl acetate, only nontoxic and unreactive side products are obtained, such as ethyl acetate when using ethoxyvinyl acetate;

g) increased enzyme activity is observed in some cases over that observed using vinyl acetate;

h) the presence of the R$^2$ and R$^3$ groups makes enol esters sterically more demanding than vinyl acetate, often resulting in increased stereoselectivity; and i) R$^2$, and particularly R$^3$ can be chiral groups.

With respect to point (i) supra, non-racemic chiral acetylenes R$^2$—C≡C—O—R$^{3*}$ (where R$^{3*}$ is a chiral group) can be employed in the synthesis of the enol esters instead of ethoxyacetylene using the methods described, for example, in Kita I, supra. Use of chiral R$^2$ and R$^3$ groups therefore allows the possibility of double stereoselection, induced both by the enzyme catalyst and by the chiral groups R$^{2*}$ and R$^{3*}$. For some substrates this can provide great advantages when only unsatisfactory enzymatic stereodifferentiation might otherwise be achieved.

In the acylation reaction, the ester of formula I is cleaved into a carboxylic acid and an alkoxy alkenol. The alkoxy alkenol immediately tautomerizes into the corresponding alkyl ester, completely precluding the possibility of reversibility of the reaction. The enzyme catalyzed acylation occurs rapidly and in high yield, and when a racemic or prochiral substrate is used the acylation is highly stereoselective, i.e. only one acylated enantiomer is formed, with the other enantiomer remaining unchanged in the reaction mixture. The process according to the invention is particularly suitable for the resolution of alcohols having a C—C double or triple bond in the β-position to the OH group, or having an epoxide or other double bond equivalent such as a cyclopropyl ring in this position.

The preferred procedure for carrying out the invention involves adding an enol ester of formula I to a solution in an organic solvent, followed by addition of the enzyme and the alcohol to be acylated. In a preferred embodiment, the enol ester is ethoxyvinyl acetate. The organic solvents used are preferably nonpolar, and preferably are ethers, such as diisopropyl ether or t-butyl methyl ether (TBME), or hydrocarbons such as isohexane, pentane or hexane. The concentration of the enol ester in the organic solvent depends upon the solubility of the alcohol and enol ester substrates and can be between about 0.05% and 50%, preferably between about 1% and about 10%. The alcohol to be acylated is similarly present at a concentration from about 0.05% to about 50%, but preferably between abut 1% and about 20%. The molar ratio of enol ester to alcohol can be 0.5:1 for racemic alcohols, i.e. 0.5 equivalents for the quantitative reaction of one enantiomer. Alternatively, the enol ester may also be employed in a large excess, for example a 100-fold molar excess in situations when, for example, unreactive alcohols are to be acylated or low amounts of enzyme are to be used. Preferred stoichiometries are between about 1 and about 10 equivalents of the enol ester relative to the alcohol.

The enzymes employed are preferably lipases, and preferably also are commercially available. Particularly preferred lipases include the lipoprotein lipases from Pseudomonas, especially the enzyme from *Pseudomonas cepacia* (formerly *P. fluorescens*), which is commercially available under the name lipase PS (formerly also P or FP) from Amano Pharmaceuticals (Nagoya, Japan). Lipases from Candida, particularly *Candida rugosa* and *Candida antarctica* (SP 625, Novo Industrie, Bagsvaerd, Denmark) are also highly suitable. The enzyme can be employed in free form or immobilized form. Methods for immobilizing enzymes are well known to those of skill in the art. A column process may be used for both free and immobilized enzymes. The quantity of enzyme is selected as a function of the size of the batch, of the reactivity of the alcohol, of the desired reaction time, and of the free or immobilized nature of the enzyme. Determining the quantity of enzyme is readily carried by simple preliminary experiments where the reaction is carried out on a pilot scale.

The transesterification reaction is carried out at between about −10° C. to about 80° C., preferably about 15° C. to about 40° C. It is preferred that the solution be stirred during the reaction. The reaction time varies, depending on the nature of the alcohol employed and on the amount of enzyme and solvent, and is usually only a few hours, but may be up to 2 weeks. Progress of the reaction is conveniently carried out using any method known to those skilled in the art of organic synthesis, including thin layer chromatography (TLC) and HPLC.

The racemic, prochiral or other alcohols to be acylated are commercially available or can be prepared by processes well-known to those skilled in the art, or by methods readily available in the chemical literature. The enol esters used in the process are not commercially available, but can easily be prepared from the corresponding alkoxyacetylenes. See, for example, Kita I, supra. For example, commercially available ethoxyacetylene is used as a starting material to prepare ethoxyvinyl acetate. Purification of the enol ester may be carried out, for example, by distillation or by silica gel chromatography. Purity of the product can easily be checked by NMR spectroscopy or gas chromatography.

The products formed in the process are separated in a straightforward manner. The ethyl acetate obtained in an acylation using ethoxyvinyl acetate distills off easily. Excess acylating reagent as well as alcohol and acyl alcohol can also be separated by distillation, but is more usually separated by simple chromatography or via extraction or crystallization. The free alcohols can be liberated from the acylated alcohols by methods well known to those skilled in the art of organic synthesis, such as by basic hydrolysis. The enzyme catalyst used in the reaction can easily be recovered by filtration, and may be used repeatedly.

The present invention, thus generally described, will be understood more readily by reference to the following examples, which are provided by way of illustration and are not intended to be limiting of the present invention.

EXAMPLE 1

General Procedure for Enzymatic Acylation with Ethoxyvinyl Acetate

The alcohol to be acylated is dissolved or suspended in a 10% v/v solution of the enol acetate in hexane or t-butylmethyl ether. Lipase PS (10% enzyme by weight) is added in free or immobilized form and the mixture is stirred at room temperature. Progress of the reaction is monitored by thin-layer chromatography (TLC) using, for example, a mobile phase of ethyl acetate/hexane, adjusted to produce appropriate rf differences between the free alcohol and its acylated form. When reaction is complete as determined by TLC (i.e. complete acylation in the case of simple and prochiral alcohols, or 50% conversion in the case of racemic alcohols), the enzyme is separated by filtration and the residual solution is concentrated in vacuo. When a racemic alcohol is employed the resulting alcohol/ester mixture is preferably separated by column chromatography on silica gel, or by extraction, crystallization, or distillation.

Lipase SP 625 from *Candida antarctica* can be substituted for the lipase PS, with similar results. The relative rates of reaction observed between the two lipases was found to be substrate-dependent.

EXAMPLE 2

Acetylation of 1-Phenylethanol

1-Phenylethanol (100 mg) was dissolved in a 10% solution of ethoxyvinyl acetate in hexane (2 ml), followed by addition of lipase PS (10 mg). After about 3 hours at room temperature, 50% conversion was observed by TLC. The alcohol and acetate were isolated using flash chromatography on silica gel 60 using a 1:10 to 1:1 gradient of ethyl acetate in hexane. The isolated yield of the acetate was 40%, corresponding to 80% of the theoretical maximum at 50% conversion, and that of the alcohol 39%. The enantiomeric excess (ee) of the acetate was >95% (determined by $^1$H-NMR, chiral shift experiment with Eu(hfc)$_3$, 10 mg of acetate, 40 mg of shift reagent); $\alpha_D$ +103.5° (c=1, MeOH).

EXAMPLE 3

Acetylation of 1-buten-3-ol

The reaction was carried out as in Example 2 except that a reaction time of 24 hours was used. The yield of acetate was 31%, ee 70% ($^1$H-NMR).

EXAMPLE 4

Acetylation of Pantolactone

The reaction was carried out as in Example 2 except that the solvent was TBME and the reaction time was 44 hours. The respective yields of acetate and alcohol after chromatographic separation were 42% and 41%. Specific rotations were not accurately determined due to the presence of impurities.

EXAMPLE 5

Acetylation of Allethrolone

The reaction was carried out as in Example 2 except that the reaction time was 10 hours. The yield of acetate was 45% and that of the alcohol 46%. The acetate had 89% ee ($^1$H-NMR, shift experiment performed as in Example 2).

EXAMPLE 6

Acetylation of 2-(1-Naphthylmethyl)propane-1,3-diol

The reaction was carried out as in Example 2 except the reaction temperature was 5° C., the solvent was 1:1 dimethoxyethane/diisopropylether, and the reaction time was 10 hours. The conversion was 94%, and the acetate had a 94% ee ($^1$H-NMR, shift experiment as Example 2).

EXAMPLE 7

Acetylation of Geraniol

The reaction was carried out as in Example 2 except that the reaction time was 1 hour and the reaction temperature was 35° C. Acylation was 100% complete as determined by TLC.

EXAMPLE 8

Non-enzyme-catalyzed Enol Ester Cleavage

A 10% solution of ethoxyvinyl acetate in hexane (2 ml) was mixed at room temperature with either phenylethanol or allethrolone (10% by volume). Both alcohols are readily acylated under enzyme-catalyzed conditions. After 5 hours at RT (21° C.), no acylation products could be detected by TLC in either case.

EXAMPLE 9

Acylation with Ethyl Acetate

The reaction was carried out as in Example 8, except that ethyl acetate was used in place of ethoxyvinyl acetate, and 20 mg of enzyme lipase PS was added. No acylation products could be detected after 2 hours by TLC.

EXAMPLE 10

Use of Lipase *Candida antarctica*

The reaction was carried out as in Example 2 except that the *C. antarctica* was used. 50% conversion was observed after about 2 hours.

What is claimed is:

1. A method for the enzyme catalyzed acylation of alcohols, comprising contacting a mixture of an ester and an alcohol with a lipase, wherein said ester has the formula I

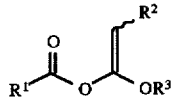

wherein $R^1$ is hydrogen, $C_1$–$C_{18}$-alkyl which is optionally substituted by halogen, phenyl or ($C_1$–$C_3$)-alkoxy ($C_1$–$C_4$)-alkyl, $R^2$ is hydrogen or E- or Z-methyl, and $R^3$ is methyl, ethyl, propyl, isopropyl or n-butyl;

and said alcohol has a formula selected from the group consisting of formulas II and IV

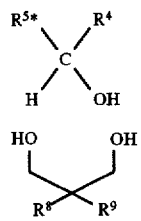

wherein $R^4$ is optionally halogen-substituted $C_1$–$C_{18}$-alkyl or $C_3$–$C_{10}$-cycloalkyl, $R^5$ is 2-epoxy-$C_1$–$C_5$-alkyl, or $R^5$ is $C_1$–$C_{10}$-alkyl, $C_2$–$C_{10}$-alkenyl, $C_2$–$C_{10}$-alkynyl or $C_3$–$C_8$-cycloalkenyl, optionally substituted with COOH, halogen, $NO_2$, CN, $C_1$–$C_4$-alkoxycarbonyl or phenyl, said phenyl group being optionally substituted with halogen, $NO_2$, CN or $C_1$–$C_4$-alkoxy, or $R^5$ is aryl or heteroaryl, optionally substituted, with $C_1$–$C_4$-alkyl, $C_1$–$C_4$-alkoxy, halogen, $NO_2$, CN, or a protected amino group, or wherein $R^4$ and $R^5$ together form an alkenyl group having the formula III

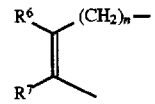

wherein n is 1, 2, or 3, and $R^6$ and $R^7$ are the same or different and each is hydrogen, $C_1$–$C_4$-alkyl, or $C_2$–$C_4$ alkenyl, $R^6$ and $R^7$ taken together are fused phenyl or fused naphthyl, optionally substituted with $C_1$–$C_4$-alkyl-, $C_1$–$C_4$-alkoxy-, $NO_2$—, CN— or halogen, and where the alkenyl group of formula III may optionally contain a keto group;

$R^8$ is hydrogen or a $C_1$–$C_{18}$ alkyl group, $R^9$ is $C_1$–$C_{18}$ alkyl, aralkyl, aryl, benzyl, naphthylmethyl or O-($C_1$–$C_{18}$)-alkyl, O-aralkyl, O-aryl, O-benzyl or O-naphthylmethyl, and subsequently isolating the resulting acylated reaction product.

2. The method of claim 1, wherein said lipase is selected from the group consisting of lipases isolated from porcine liver, porcine pancreas, and microbials.

3. The method of claim 2, wherein said microbial lipase is isolated from a microorganism selected from the group consisting of Mucor, Rhizopus, Penicillium, Aspergillus, Candida, and Pseudomonas.

4. The method of claim 1, wherein $R^1$ is $C_1$–$C_4$-alkyl, which is optionally chlorine-substituted.

5. The method of claim 1, wherein $R^4$ is $C_1$–$C_7$-alkyl, which is optionally chlorine-substituted, or $R^4$ is $C_3$–$C_5$-cycloalkyl.

6. The method of claim 1, wherein $R^1$ is $C_1$–$C_4$-alkyl, $C_2$–$C_4$-alkenyl or $C_2$–$C_4$-alkynyl, said alkyl, alkenyl or alkynyl radicals optionally being phenyl-substituted.

7. The method of claim 1, wherein $R^5$ is phenyl, naphthyl, phenanthryl, furyl, thienyl, pyrrolyl or pyridyl, optionally substituted with halogen, $NO_2$, CN, $C_1$–$C_4$-alkyl or $C_1$–$C_4$-alkoxy.

8. The method of claim 1, wherein $R^6$ and $R^7$ together form fused phenyl.

9. The method of claim 1, wherein $R^1$ is methyl or chloromethyl.

10. The method of claim 1, wherein $R^4$ is which is optionally chlorine-substituted $C_1$–$C_5$-alkyl or $R^4$ is cyclopropyl.

11. The method of claim 1, wherein $R^5$ is phenyl, naphthyl, phenanthryl, furyl or pyridyl, optionally substituted by $NO_2$ or methoxy.

12. The method of claim 3, wherein said lipase is isolated from Pseudomonas.

13. The method of claim 12, wherein said lipase is isolated from *Pseudomonas cepacia*.

14. The method of claim 3, wherein said lipase is isolated from Candida.

15. The method of claim 14, wherein said lipase is isolated from *Candida antarctica*.

16. The method of claim 1, wherein said ester is methoxyvinyl acetate or ethoxyvinyl acetate.

17. A method for the preparation of enantiomerically enriched alcohols, comprising contacting a mixture of an ester and an alcohol with a lipase, wherein said ester has the formula I

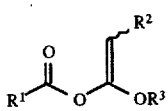

wherein $R^1$ is hydrogen, $C_1$–$C_{18}$-alkyl which is optionally substituted by halogen, phenyl or ($C_1$–$C_3$)-alkoxy ($C_1$–$C_4$)-alkyl, $R^2$ is hydrogen or E- or Z-methyl, and $R^3$ is methyl, ethyl, propyl, isopropyl or n-butyl;

and said alcohol has a formula selected from the group consisting of formulas II and IV

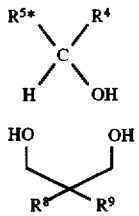

wherein $R^4$ is optionally halogen-substituted $C_1$–$C_{18}$-alkyl or $C_3$–$C_{10}$-cycloalkyl, $R^5$ is 2-epoxy-$C_1$–$C_5$-alkyl, or $R^5$ is $C_1$–$C_{10}$-alkyl, $C_2$–$C_{10}$-alkenyl, $C_2$–$C_{10}$-alkynyl or $C_3$–$C_8$-cycloalkenyl, optionally substituted with COOH, halogen, $NO_2$, CN, $C_1$–$C_4$-alkoxycarbonyl or phenyl, said phenyl group being optionally substituted with halogen, $NO_2$, CN or $C_1$–$C_4$-alkoxy, or $R^5$ is aryl or heteroaryl, optionally substituted with $C_1$–$C_4$-alkyl, $C_1$–$C_4$-alkoxy, halogen, $NO_2$, CN, or a protected amino group, or wherein $R^4$ and $R^5$ together form an alkenyl group having the formula III

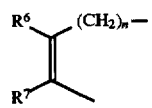

wherein n is 1, 2, or 3, and $R^6$ and $R^7$ are the same or different and each is hydrogen, $C_1$–$C_4$-alkyl, or $C_2$–$C_4$ alkenyl, $R^6$ and $R^7$ taken together are fused phenyl or fused naphthyl, optionally substituted with $C_1$–$C_4$-alkyl-, $C_1$–$C_4$-alkoxy-, $NO_2$—, CN— or halogen, and where the alkenyl group of formula III may optionally contain a keto group;

$R^8$ is hydrogen or a $C_1$–$C_{18}$ alkyl group, $R^9$ is $C_1$–$C_{18}$ alkyl, aralkyl, aryl, benzyl, naphthylmethyl or O-($C_1$–$C_{18}$)-alkyl, O-aralkyl, O-aryl, O-benzyl or O-naphthylmethyl, and subsequently isolating the resulting enantiomerically enriched alcohol of Formula II or IV.

18. A method for the preparation of enantiomerically enriched alcohols, comprising contacting a mixture of an ester and an alcohol with a lipase, wherein said ester has the formula I

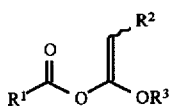

wherein $R^1$ is hydrogen, $C_1$–$C_{18}$-alkyl which is optionally substituted by halogen, phenyl or ($C_1$–$C_3$)-alkoxy ($C_1$–$C_4$)-alkyl, $R^2$ is hydrogen or E- or Z-methyl, and $R^3$ is methyl, ethyl, propyl, isopropyl or n-butyl;

and said alcohol has a formula selected from the group consisting of formulas II and IV

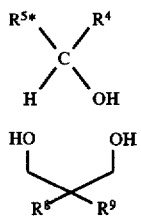

wherein $R^4$ is optionally halogen-substituted $C_1$–$C_{18}$-alkyl or $C_3$–$C_{10}$-cycloalkyl, $R^5$ is 2-epoxy-$C_1$–$C_5$-alkyl, or $R^5$ is $C_1$–$C_{10}$-alkyl, $C_2$–$C_{10}$-alkenyl, $C_2$–$C_{10}$-alkynyl or $C_3$–$C_8$-cycloalkenyl, optionally substituted with COOH, halogen, $NO_2$, CN, $C_1$–$C_4$-alkoxycarbonyl or phenyl, said phenyl group being optionally substituted with halogen, $NO_2$, CN or $C_1$–$C_4$-alkoxy, or $R^5$ is aryl or heteroaryl, optionally substituted with $C_1$–$C_4$-alkyl, $C_1$–$C_4$-alkoxy, halogen, $NO_2$, CN, or a protected amino group, or wherein $R^4$ and $R^5$ together form an alkenyl group having the formula III

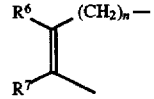

wherein n is 1, 2, or 3, and $R^6$ and $R^7$ are the same or different and each is hydrogen, $C_1$–$C_4$-alkyl, or $C_2$–$C_4$ alkenyl, $R^6$ and $R^7$ taken together are fused phenyl or fused naphthyl, optionally substituted with $C_1$–$C_4$-alkyl-, $C_1$–$C_4$-alkoxy-, $NO_2$—, CN— or halogen, and where the alkenyl group of formula III may optionally contain a keto group;

$R^8$ is hydrogen or a $C_1$–$C_{18}$ alkyl group, $R^9$ is $C_1$–$C_{18}$ alkyl, aralkyl, aryl, benzyl, naphthylmethyl or O-($C_1$–$C_{18}$)-alkyl, O-aralkyl, O-aryl, O-benzyl or O-naphthylmethyl, isolating the resulting enantiomerically enriched acylated reaction product, and removing the acyl group to provide the optically enriched alcohol.

19. The method of claim 18, wherein said acyl group is removed by base-catalyzed hydrolysis.

* * * * *